(12) United States Patent
Nishiguchi et al.

(10) Patent No.: US 9,090,530 B1
(45) Date of Patent: Jul. 28, 2015

(54) METHOD FOR PRODUCING 1,2-DICHLORO-3,3,3-TRIFLUOROPROPENE

(71) Applicant: CENTRAL GLASS COMPANY, LIMITED, Ube, Yamaguchi (JP)

(72) Inventors: Yoshio Nishiguchi, Kawagoe (JP); Satoru Okamoto, Kawagoe (JP); Fuyuhiko Sakyu, Kawagoe (JP)

(73) Assignee: CENTRAL GLASS COMPANY, LIMITED, Ube, Yamaguchi (JP)

( * ) Notice: Subject to any disclaimer, the term of this patent is extended or adjusted under 35 U.S.C. 154(b) by 0 days.

(21) Appl. No.: 14/663,418

(22) Filed: Mar. 19, 2015

Related U.S. Application Data

(63) Continuation of application No. PCT/JP2013/075540, filed on Sep. 20, 2013.

(30) Foreign Application Priority Data

Sep. 21, 2012 (JP) ................................. 2012-207928

(51) Int. Cl.
*C07C 17/25* (2006.01)
*C07C 17/23* (2006.01)

(52) U.S. Cl.
CPC ................. *C07C 17/25* (2013.01); *C07C 17/23* (2013.01)

(58) Field of Classification Search
CPC ............................... C07C 17/25; C07C 17/23
USPC .................................................. 570/157, 156
See application file for complete search history.

(56) References Cited

U.S. PATENT DOCUMENTS

| 2,739,987 A | 3/1956 | Ruh et al. |
| 2005/0090698 A1 | 4/2005 | Merkel et al. |
| 2005/0119512 A1 | 6/2005 | Du Boisson et al. |

FOREIGN PATENT DOCUMENTS

| JP | 2001-322955 A | 11/2001 |
| JP | 2006-525339 A | 11/2006 |
| JP | 2010-215659 A | 9/2010 |
| WO | 2012/112827 A2 | 8/2012 |

OTHER PUBLICATIONS

A. L. Henne et al., "A New Method of Synthesizing Organic 1,1,1-Trifluorides," Journal of American Chemical Society, Dec. 1941, pp. 3478-3479, vol. 63.
A. M. Whaley et al., "Isomerization During Allylic Fluorination," Journal of American Chemical Society, Mar. 1948, pp. 1026-1027, vol. 70.
R. N. Haszeldine et al., "Reactions of Fluorocarbon radicals. Part V. Alternative syntheses for trifluouromethylacetylene (3:3:3-trifluoropropyne) and influence of poly-fluoro-groups on adjacent hydrogen and halogen atoms," Journal of the Chemical Society, 1951, pp. 2495-2504.
Tarrant et al., "Free radical additions invloving fluorine compounds. IV. The addition of dibromodifluoromethane to some fluoroolefins," J. Am. Chem. Soc., May 20, 1955, 77, pp. 2783-2787.
International Search Report issued on Oct. 29, 2013 regarding PCT/JP2013/075540.
Written Opinion of the International Searching Authority issued on Oct. 29, 2013 regarding PCT/JP2013/075540.

*Primary Examiner* — Elvis O Price
(74) *Attorney, Agent, or Firm* — Lowe Hauptman & Ham, LLP

(57) ABSTRACT

A method for producing 1,2-dichloro-3,3,3-trifluoropropene of the present invention includes reacting 1,2-dichloro-1-halogeno-3,3,3-trifluoropropane with a base in a liquid phase; and extracting generated 1,2-dichloro-3,3,3-trifluoropropene to the outside of a reaction system to recover while the reaction is continued. According to the present invention, 1,2-dichloro-3,3,3-trifluoropropene is obtained at a high yield by a simple method. Thus, 1,2-dichloro-3,3,3-trifluoropropene is produced in an industrial scale.

4 Claims, No Drawings

METHOD FOR PRODUCING 1,2-DICHLORO-3,3,3-TRIFLUOROPROPENE

CROSS REFERENCE TO RELATED APPLICATION

This application is based upon and claims the benefit of priority from Japanese Patent Applications No. 2012-207928 filed on Sep. 21, 2012 and the prior PCT Application PCT/JP2013/075540 filed on Sep. 20th, 2013, the entire contents of which are incorporated herein by reference.

FIELD

The present invention relates to a method for producing 1,2-dichloro-3,3,3-trifluoropropene.

BACKGROUND 1,2-dichloro-3,3,3-trifluoropropene includes an unsaturated bond, and is expected to provide a function of a cleaner or a coolant as hydrochlorofluorocarbon (HCFC), which is relatively easily decomposed in the atmosphere.

There are various known methods for producing 1,2-dichloro-3,3,3-trifluoropropene. For example, A. L. Henne et al., J. Am. Chem. Soc., 1941, pp. 3478-3479 discloses a method of reacting 1,2,3,3,3-pentachloropropene with antimony trifluoride in a liquid phase.

A. M. Whaley et al., J. Am. Chem. Soc., 1948, pp. 1026-1027 discloses a method of reacting 1,1,2,3,3-pentachloropropene and antimony trifluoride with adding antimony pentachloride in a liquid phase. R. N. Haszeldine et al., J. Chem. Soc., 1951, pp 2495-2504 discloses a method of adding potassium hydroxide in a solid state to 1,2,2,-trichloro-3,3,3-trifluoropropane in a liquid state and refluxing, while heating, the resultant substance to produce 1,2-dichloro-3,3,3-trifluoropropene.

Regarding a reaction of 1,2-dichloro-3,3,3-trifluoropropene, U.S. Pat. No. 2,739,987 discloses that a reaction of 1,2-dichloro-3,3,3-trifluoropropene with methanol in the presence of potassium hydroxide generates 1-chloro-2-methoxy-3,3,3-trifluoropropene.

WO2012/112827 discloses that a reaction of 1,2-dichloro-3,3,3-trifluoropropene with a base generates 1-chloro-3,3,3-trifluoropropyne.

According to the production method described in R. N. Haszeldine et al., J. Chem. Soc., 1951, pp 2495-2504, powdery potassium hydroxide is dispersed in 1,2,2-trichloro-3,3,3-trifluoropropane in a liquid state to cause a reaction. However, the yield is low (48%) and the reaction is not uniform. Therefore, this method is not considered to be efficient as an industrial production method.

As can be seen from the above, it has been desired to establish a method for producing 1,2-dichloro-3,3,3-trifluoropropene, which is a target compound of the present invention, easily and in an industrial scale.

SUMMARY

As a result of accumulating active studies to solve the above-described problem, the present inventors found that 1,2-dichloro-3,3,3-trifluoropropene is obtained at a high yield by reacting 1,2-dichloro-1-halogeno-3,3,3-trifluoropropane with a base in a liquid phase and extracting the generated 1,2-dichloro-3,3,3-trifluoropropene to the outside of the reaction system to recover, and thus achieved the present invention.

Namely, the present invention is as follows.

[Invention 1]
A method for producing 1,2-dichloro-3,3,3-trifluoropropene, including reacting 1,2-dichloro-1-halogeno-3,3,3-trifluoropropane represented by formula [1] as shown below with a base in a liquid phase; and extracting the generated 1,2-dichloro-3,3,3-trifluoropropene to the outside of a reaction system to recover while the reaction is continued:

[Chemical Formula 1]
Formula [1]:

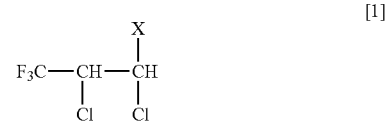

(in the formula, X represents fluorine, chlorine or bromine).

According to the invention 1, the reaction of 1,2-dichloro-1-halogeno-3,3,3-trifluoropropane is suppressed from being advanced to generate a propyne such as 1-chloro-3,3,3-trifluoropropyne or the like and the reaction can be stopped in the state where an alkene compound is generated. Therefore, generation of byproducts, which are not 1,2-dichloro-3,3,3-trifluoropropene, can be suppressed, and 1,2-dichloro-3,3,3-trifluoropropene can be obtained at a higher yield.

[Invention 2]
A method according to invention 1, wherein the reaction of the 1,2-dichloro-1-halogeno-3,3,3-trifluoropropane with the base is caused with neither a phase transfer catalyst nor a compatibilizer being present. The expression "neither a phase transfer catalyst nor a compatibilizer being present" indicates that each of the phase transfer catalyst and the compatibilizer is contained at a content in the range lower than or equal to 0.01% by mass that includes zero (0).

According to the invention 2, in the reaction of 1,2-dichloro-1-halogeno-3,3,3-trifluoropropane with the base, generation of byproducts, which are not 1,2-dichloro-3,3,3-trifluoropropene, can be suppressed, and 1,2-dichloro-3,3,3-trifluoropropene can be obtained at a higher yield.

[Invention 3]
A method according to invention 1 or 2, wherein the base is at least one inorganic base selected from the group consisting of alkaline metal alkoxides, carbonates of alkaline metals, carbonates of alkaline earth metals, hydroxides of alkaline metals, and hydroxides of alkaline earth metals.

[Invention 4]
A method according to any one of inventions 1 through 3, wherein the 1,2-dichloro-1-halogeno-3,3,3-trifluoropropane is 1,1,2-trichloro-3,3,3-trifluoropropane.

DESCRIPTION OF EMBODIMENTS

Hereinafter, the present invention will be described in more detail. The present invention is directed to a method for producing 1,2-dichloro-3,3,3-trifluoropropene, by which 1,2-dichloro-1-halogeno-3,3,3-trifluoropropane is reacted with a base in a liquid phase, and 1,2-dichloro-3,3,3-trifluoropropene generated by the reaction is extracted to the outside of the reaction system to be recovered, while the reaction is continued.

The present invention is not limited to the description of this specification, and may be carried out in embodiments other than the following embodiments. The following embodiments may be optionally modified without departing from the gist of the present invention. All the publications cited in this specification, for example, prior art documents, laid-open publications, patent publications and other patent documents are incorporated herein by reference.

1,2-dichloro-1-halogeno-3,3,3-trifluoropropane, which is a starting material of the present invention, is represented by the following formula [1].

[Chemical Formula 2]

Formula [1]:

(in the formula, X represents fluorine, chlorine or bromine).

Specific compounds usable as 1,2-dichloro-1-halogeno-3,3,3-trifluoropropane include 1,1,2-trichloro-3,3,3-trifluoropropane, 1,2-dichloro-1,3,3,3-tetrafluoropropane, and 1-bromo-1,2-dichloro-3,3,3-trifluoropropane. Among these compounds, 1,1,2-trichloro-3,3,3-trifluoropropane is preferably usable for easy availability thereof and usefulness of a resultant compound. In the case where 1,1,2-trichloro-3,3,3-trifluoropropane is used as the material, hydrogen chloride, which is generated together with 1,2-dichloro-3,3,3-trifluoropropene, can be industrially used.

According to the method for producing 1,2-dichloro-3,3,3-trifluoropropene of the present invention, the reaction is caused in a liquid phase. 1,2-dichloro-1-halogeno-3,3,3-trifluoropropane, which is a starting material of the present invention, is in a liquid state at room temperature and normal pressure, and therefore does not need to be supplied with a solvent. Needless to say, the reaction may be caused with a solvent.

Generally in a dehydrohalogenation reaction, a phase transfer catalyst and/or a compatibilizer is occasionally used as an additive in order to promote a reaction of a starting material in an organic phase with a base in an aqueous phase. In the method for producing 1,2-dichloro-3,3,3-trifluoropropene according to the present invention, a phase transfer catalyst and/or a compatibilizer may be used as an additive in addition to a solvent. However, it is preferable that the method according to the present invention is performed with neither a phase transfer catalyst nor a compatibilizer being present, for the following reason. If the method according to the present invention is performed in the presence of a phase transfer catalyst and/or a compatibilizer, a reaction byproduct is generated and thus the purity of the target compound is decreased, and also the generated 1,2-dichloro-3,3,3-trifluoropropene is dissolved in the aqueous phase and thus is made difficult to be recovered. When 1,2-dichloro-1-halogeno-3,3,3-trifluoropropane is reacted with a base with neither a phase transfer catalyst nor a compatibilizer being present in the present invention, generation of a reaction byproduct such as 1-chloro-3,3,3-trifluoropropyne or the like can be suppressed, and also the generated 1,2-dichloro-3,3,3-trifluoropropene can be recovered efficiently. Therefore, 1,2-dichloro-3,3,3-trifluoropropene can be obtained at a high selectivity and a high yield.

The term "phase transfer catalyst" refers to a "substance having a function of, in a reaction system of an aqueous phase containing nucleophilic anion and a non-polar organic phase containing an organic substrate reactive with the aqueous phase, exchanging the nucleophilic anion that is present in the aqueous phase with anion of itself and moving between the aqueous phase and the organic phase to transfer the nucleophilic anion to the organic substrate that is present in the organic phase, thus to promote a reaction". Substances usable as the "phase transfer catalyst" include, for example, crown ether, cryptand, and onium salt, which are generally known. The term "compatibilizer" refers to a "substance that decreases the surface tension of substances that are non-compatible with each other, thus to increase the compatibility". Substances usable as the "compatibilizer" include, for example, methanol, ethanol, and propanol, which are generally known.

It is preferable to use, as the base for the reaction, a hydroxide of an alkaline metal or a hydroxide of an alkaline earth metal, which are both economical and easy to handle. The term "alkaline metal" refers to lithium, sodium, potassium, rubidium or cesium. The term "alkaline earth metal" refers to magnesium, calcium or strontium.

Specific examples of the hydroxide of the alkaline metal and the hydroxide of the alkaline earth metal include compounds such as lithium hydroxide, sodium hydroxide, potassium hydroxide, calcium hydroxide, magnesium hydroxide, strontium hydroxide, and the like. Among these compounds, potassium hydroxide, sodium hydroxide, calcium hydroxide, and magnesium hydroxide are preferable. Potassium hydroxide and sodium hydroxide, which are low-cost and industrially available in a large amount, are especially preferable. Also, it is preferable to use, as the base for the reaction, a carbonate of an alkaline metal or a carbonate of an alkaline earth metal. Additionally, it is preferable to use, as the base for the reaction, an alkaline metal alkoxide. Specific examples of the alkaline metal alkoxide include compounds such as sodium methoxide, sodium ethoxide, and the like.

According to the present invention, one type of base may be used or two or more types of bases may be combined.

According to the present invention, the base needs to be used in an amount that is at least 1 mol with respect to 1 mol of 1,2-dichloro-1-halogeno-3,3,3-trifluoropropane. Usually, the amount of the base may be optionally selected from the range higher than or equal to 1 mol and smaller than or equal to 10 mol with respect to 1 mol of the propane. The amount of the base is preferably larger than or equal to 1 mol and smaller than or equal to 4 mol, and more preferably larger than or equal to 1 mol and smaller than or equal to 2 mol. It is possible to use the base in an amount larger than 10 mol with respect to 1 mol of 1,2-dichloro-1-halogeno-3,3,3-trifluoropropane, but there is no advantage of using the base in such a large amount.

In the case where the amount of the base is less than 1 mol with respect to 1 mol of 1,2-dichloro-1-halogeno-3,3,3-trifluoropropane in the present invention, the ratio of conversion realized by the reaction may be decreased. In such a case, an unreacted 1,2-dichloro-1-halogeno-3,3,3-trifluoropropane may be recovered in a purification step after the reaction and recycled for a subsequent reaction.

According to the method for producing 1,2-dichloro-3,3,3-trifluoropropene of the present invention, 1,2-dichloro-1-halogeno-3,3,3-trifluoropropane is reacted with a base in a liquid phase. 1,2-dichloro-1-halogeno-3,3,3-trifluoropropane, which is a starting material of the present invention, is in a liquid state at room temperature and normal pressure, and therefore does not need to be supplied with a solvent.

According to the present invention, in the case where the base is solid at room temperature and normal pressure, the base may be supplied with water as a solvent and used in the form of an aqueous solution in order to make the reaction operation easier. The concentration of the aqueous solution may be optionally adjusted by a person of ordinary skill in the art such that the reaction advances sufficiently or such that the base is sufficiently dissolved in the solvent. A specific concentration of the aqueous solution varies in accordance with the type of compound used as the base. In the case where, for example, an aqueous solution of potassium hydroxide is used, the concentration of the aqueous solution is usually higher than or equal to 5% by mass and lower than or equal to 75% by mass, preferably higher than or equal to 10% by mass and lower than or equal to 60% by mass, and more preferably higher than or equal to 15% by mass and lower than or equal to 50% by mass.

According to the method for producing 1,2-dichloro-3,3,3-trifluoropropene of the present invention, generated 1,2-dichloro-3,3,3-trifluoropropene is extracted to the outside of the reaction system. This suppresses generation of 1-chloro-3,3,3-trifluoropropyne, which would otherwise be caused by a dehydrohalogenation reaction of 1,2-dichloro-3,3,3-trifluoropropene. The extraction of the generated 1,2-dichloro-3,3,3-trifluoropropene to the outside of the reaction system also decreases the concentration of 1,2-dichloro-3,3,3-trifluoropropene in the reaction system and thus can suppress decrease in the reaction rate.

There is no limitation on the reaction pressure. In order to extract 1,2-dichloro-3,3,3-trifluoropropene (standard boiling point: 53.7° C.), which is a product of the method, to the outside of the reaction system as gas, the operation is preferably performed at normal pressure or in a slightly pressurized state, and more preferably at atmospheric pressure.

A preferable reaction temperature is as follows. In order to extract 1,2-dichloro-3,3,3-trifluoropropene (standard boiling point: 53.7° C.), which is a product of the method, to the outside of the reaction system as gas, a preferable reaction temperature is higher than or equal to the boiling point of 1,2-dichloro-3,3,3-trifluoropropene at the above-described inner pressure of the reactor. In the case where the reaction is caused at atmospheric pressure, the reaction temperature is preferably higher than or equal to 55° C. and lower than or equal to 75° C.

In the method for producing 1,2-dichloro-3,3,3-trifluoropropene of the present invention, corrosive gas is not generated. Therefore, in the case where the reaction is caused at normal pressure or in a pressurized state, there is no specific limitation on the material of a reactor as long as the material withstands the pressure. The material of the reactor may be common stainless steel, glass, or fluorine resin. Alternatively, the reactor may be formed of a material lined with glass or fluorine resin.

A pressure-resistant reactor may be used. However, a reaction caused in a liquid phase advances without the pressure in the reaction system being much increased and may be caused at normal pressure with no specific problem. Therefore, there is no significant advantage of using a pressure-resistant reactor.

1,2-dichloro-3,3,3-trifluoropropene produced by the method according to the present invention exists in the form of a liquid at room temperature and normal pressure. Therefore, the gas obtained by the reaction of 1,2-dichloro-1-halogeno-3,3,3-trifluoropropane with a base, namely, the generated 1,2-dichloro-3,3,3-trifluoropropene may be extracted to the outside of the reaction system, caused to flow in a cooled condenser to be condensed, and precision-distilled, so that highly pure 1,2-dichloro-3,3,3-trifluoropropene is obtained. 1,2-dichloro-3,3,3-trifluoropropene generated by the reaction is a mixture of geometric isomers such as cis and trans isomers. Nonetheless, the mixture can be precision-distilled to provide highly pure cis-1,2-dichloro-3,3,3-trifluoropropene and trans-1,2-dichloro-3,3,3-trifluoropropene. The present inventors found that in the case where 1,2-dichloro-3,3,3-trifluoropropene generated by the reaction of 1,2-dichloro-1-halogeno-3,3,3-trifluoropropane with a base is extracted to the outside of the reaction system and recovered, generation of 1-chloro-3,3,3-trifluoropropyne, which is a byproduct, is significantly suppressed, and 1,2-dichloro-3,3,3-trifluoropropene, which is the target compound, is obtained at a high yield.

According to the present invention, extraction of the generated 1,2-dichloro-3,3,3-trifluoropropene to the outside of the reaction system is preferably performed continuously or semi-continuously, as can be optionally adjusted by a person of ordinary skill in the art.

EXAMPLES

Hereinafter, the present invention will be described in more detail by way of examples. The present invention is not limited to the following examples. Herein, "%" used for a composition analysis value represents the "surface area %" of each of components of a reaction mixture measured by direct use of gas chromatography (unless otherwise specified, the detector is FID).

In the examples, the expression "composition containing 1,1,2-trichloro-3,3,3-trifluoropropane" refers to a mixture of a reaction product containing 1,1,2-trichloro-3,3,3-trifluoropropane as a main component, an unreacted material, and a reaction byproduct. The expression "composition containing 1,2-dichloro-3,3,3-trifluoropropene" refers to a mixture of a reaction product containing 1,2-dichloro-3,3,3-trifluoropropene as a main component, an unreacted material, and a reaction byproduct.

In each of examples 1 through 5 described below, 1,2-dichloro-3,3,3-trifluoropropene was produced by use of, as a material compound, a compound represented by formula [1] identified above in which X was Cl (1,1,2-trichloro-3,3,3-trifluoropropane).

Example 1

Example in which Neither a Compatibilizer Nor a Phase Transfer Catalyst was Used A 1000 ml glass reactor equipped with a gas introduction inlet was cooled in an iced water bath of 0° C., and was supplied with 554.1 g (4.24 mol) of trans-1-chloro-3,3,3-trifluoropropene. While the reactor was cooled in the iced water bath of 0° C., chlorine was introduced into the reactor at 0.8 g/min., and the reactor was irradiated with light by use of a high-pressure mercury lamp provided outside the reactor. The organic substance supplied as the material compound and chlorine in the reactor were stirred by a magnetic stirrer. After chlorine was introduced for six hours, the light irradiation by use of the high-pressure mercury lamp was stopped to finish the reaction. After the reaction was finished, the organic substance in the reactor was washed with water, a weakly alkaline aqueous solution and a saturated saline solution. As a result, 836.3 g of composition containing 1,1,2-trichloro-3,3,3-trifluoropropane was obtained.

The obtained composition was analyzed by gas chromatography to find the following composition ratio. The composition contained 1,1,2-trichloro-3,3,3-trifluoropropane at a content of 96.2%. The yield of 1,1,2-trichloro-3,3,3-trifluoropropane was 94.1%.

A 1000 ml round-bottom three-neck glass flask equipped with a dropping funnel, a glass protective tube for receiving a thermocouple, and a gas discharge tube was supplied with 893.2 g of 25% by weight of aqueous solution of potassium hydroxide (potassium hydroxide: 3.98 mol). This reactor was heated in an oil bath set at 75° C. 400 g of the above-obtained composition containing 1,1,2-trichloro-3,3,3-trifluoropropane was dropped into the reactor while being stirred by a magnetic stirrer (introduction rate: 2.2 g/min.). Highly concentrated 1,2-dichloro-3,3,3-trifluoropropene gas generated by the reaction was guided out of the reactor continuously through the gas discharge tube, condensed by a glass cooling device in which a coolant of 0° C. was circulated, and collected in a flask cooled in a dry ice-acetone bath. Three hours later, the composition containing 1,1,2-trichloro-3,3,3-trifluoropropane was entirely supplied to the reactor. After the supply of the material was finished, the reactor was heated for 30 minutes, and the collection of the composition containing 1,2-dichloro-3,3,3-trifluoropropene was finished. After the reaction was finished, the product collected in the flask provided at an exit of the cooling device was washed with water and then with a saturated saline solution. As a result, 314.7 g of composition containing 1,2-dichloro-3,3,3-trifluoropropene was obtained.

The obtained composition containing 1,2-dichloro-3,3,3-trifluoropropene was analyzed by gas chromatography to find the following composition ratio. The composition contained cis-1,2-dichloro-3,3,3-trifluoropropene at a content of 84.5% and trans-1,2-dichloro-3,3,3-trifluoropropene at a content of 7.7%. The yield of 1,2-dichloro-3,3,3-trifluoropropene (total yield of the cis isomer and the trans isomer) was 91.1%.

The obtained composition containing 1,2-dichloro-3,3,3-trifluoropropene was distilled and purified to obtain cis-1,2-dichloro-3,3,3-trifluoropropene and trans-1,2-dichloro-3,3,3-trifluoropropene.

Example 2

Example in which Neither a Compatibilizer Nor a Phase Transfer Catalyst was Used A reaction was caused in substantially the same manner as in example 1 except that 640.1 g of 25% by weight of aqueous solution of sodium hydroxide (sodium hydroxide: 4.00 mol) was used and that 400 g of composition containing 1,1,2-trichloro-3,3,3-trifluoropropane was dropped for 5 hours (introduction rate: 1.3 g/min.). As a result, 318.2 g of composition containing 1,2-dichloro-3,3,3-trifluoropropene was obtained.

The obtained composition containing 1,2-dichloro-3,3,3-trifluoropropene was analyzed by gas chromatography to find the following composition ratio. The composition contained cis-1,2-dichloro-3,3,3-trifluoropropene at a content of 84.7% and trans-1,2-dichloro-3,3,3-trifluoropropene at a content of 7.8%. The yield of 1,2-dichloro-3,3,3-trifluoropropene (total yield of the cis isomer and the trans isomer) was 93.4%.

Example 3

Example in which a Phase Transfer Catalyst was Used

A reaction was caused in substantially the same manner as in example 1 except that 4.7 g of tetrabutylammonium bromide was supplied as a phase transfer catalyst to a reactor accommodating the composition containing 1,1,2-trichloro-3,3,3-trifluoropropane. As a result, 224.7 g of composition containing 1,2-dichloro-3,3,3-trifluoropropene was obtained.

The obtained composition containing 1,2-dichloro-3,3,3-trifluoropropene was analyzed by gas chromatography to find the following compound ratio. The compound contained cis-1,2-dichloro-3,3,3-trifluoropropene at a content of 67.5%, trans-1,2-dichloro-3,3,3-trifluoropropene at a content of 9.8%, and 1-chloro-3,3,3-trifluoropropyne at a content of 12.5%. The yield of 1,2-dichloro-3,3,3-trifluoropropene (total yield of the cis isomer and the trans isomer) was 54.1%.

Example 4

Example in which a Compatibilizer was Used

A reaction was caused in substantially the same manner as in example 1 except that 167.5 g of methanol was supplied as a compatibilizer for 1,1,2-trichloro-3,3,3-trifluoropropane and an aqueous solution of the base to a reactor accommodating the composition containing 1,1,2-trichloro-3,3,3-trifluoropropane. As a result, 301.9 g of composition containing 1,2-dichloro-3,3,3-trifluoropropene was obtained.

The obtained composition containing 1,2-dichloro-3,3,3-trifluoropropene was analyzed by gas chromatography to find the following composition ratio. The composition contained cis-1,2-dichloro-3,3,3-trifluoropropene at a content of 81.8%, trans-1,2-dichloro-3,3,3-trifluoropropene at a content of 7.1%, 1-chloro-3,3,3-trifluoropropyne at a content of 0.1%, and 1-chloro-2-methoxy-3,3,3-trifluoropropene at a content of 0.3%. The yield of 1,2-dichloro-3,3,3-trifluoropropene (total yield of the cis isomer and the trans isomer) was 83.0%.

Example 5

Example in which a Compatibilizer and a Phase Transfer Catalyst were Both Used

A reaction was caused in substantially the same manner as in example 1 except that 167.5 g of methanol was supplied as a compatibilizer for 1,1,2-trichloro-3,3,3-trifluoropropane and an aqueous solution of the base, and 4.7 g of tetrabutylammonium bromide was supplied as a phase transfer catalyst, to a reactor accommodating the composition containing 1,1,2-trichloro-3,3,3-trifluoropropane. As a result, 260.4 g of composition containing 1,2-dichloro-3,3,3-trifluoropropene was obtained.

The obtained composition containing 1,2-dichloro-3,3,3-trifluoropropene was analyzed by gas chromatography to find the following composition ratio. The composition contained cis-1,2-dichloro-3,3,3-trifluoropropene at a content of 78.5%, trans-1,2-dichloro-3,3,3-trifluoropropene at a content of 9.0%, 1-chloro-3,3,3-trifluoropropyne at a content of 2.9%, and 1-chloro-2-methoxy-3,3,3-trifluoropropene at a content of 1.4%. The yield of 1,2-dichloro-3,3,3-trifluoropropene (total yield of the cis isomer and the trans isomer) was 70.9%.

The results of examples 1 through 5 are summarized in Table 1. 1,1,2-trichloro-3,3,3-trifluoropropane and potassium hydroxide, and 1,1,2-trichloro-3,3,3-trifluoropropane and sodium hydroxide, are separated from each other to form two layers and are not essentially compatible with each other. However, in examples 1 and 2 in which neither a phase transfer catalyst nor a compatibilizer was added, 1,2-dichloro-3,3,3-trifluoropropene as the target compound was obtained at a higher yield than in examples 3 through 5 in which a phase transfer catalyst and/or a compatibilizer was added.

TABLE 1

|  | Phase transfer catalyst | Compatibilizer | Yield [mol %] | |
| --- | --- | --- | --- | --- |
|  |  |  | 1223xd | Cl-TFPy |
| Example 1 | Not used | Not used | 91.1 | <0.1 |
| Example 2 | Not used | Not used | 93.4 | <0.1 |
| Example 3 | Used | Not used | 54.1 | 11.2 |
| Example 4 | Not used | Used | 83.0 | 0.1 |
| Example 5 | Used | Used | 70.9 | 3.0 |

1223xd: 1,2-dichloro-3,3,3-trifluoropropene
Cl-TFPy: 1-chloro-3,3,3-trifluoropropyne Next, in example 6, 1,2-dichloro-3,3,3-trifluoropropene was produced by use of, as a material compound, a compound represented by formula [1] identified above in which X was F (2,3-dichloro-1,1,1,3-tetrafluoropropane).

Example 6

A 1000 ml glass reactor equipped with a gas introduction inlet was cooled in a dry ice-acetone bath of −78° C., and was supplied with 901.86 g (7.90 mol) of trans-1,3,3,3-tetrafluoropropene. While the reactor was cooled at −78° C., chlorine was introduced into the reactor at an average rate of 1.70 g/min., and the reactor was irradiated with light by use of a high-pressure mercury lamp provided outside the reactor. The organic substance supplied as the material compound and chlorine in the reactor were stirred by a magnetic stirrer. Five hours and 30 minutes after the start of the reaction, the introduction of chlorine and the light irradiation by use of the high-pressure mercury lamp were stopped to finish the reaction. Chlorine was introduced in an amount of 560.5 g (7.90 mol). After the reaction was finished, the organic substance in the reactor was washed with water, an aqueous solution of saturated sodium hydrogen carbonate and a saturated saline solution. As a result, 1427.0 g of composition containing 2,3-dichloro-1,1,1,3-tetrafluoropropane (HCFC-234da) was obtained. The obtained composition was analyzed by gas chromatography to find the following composition ratio. The composition contained 2,3-dichloro-1,1,1,3-tetrafluoropropane at a content of 98.7% (total of diastereomer). The yield of 2,3-dichloro-1,1,1,3-tetrafluoropropane was 96.3%.

A 2000 ml round-bottom three-neck glass flask equipped with a dropping funnel, a glass protective tube for receiving a thermocouple, and a gas discharge tube was supplied with 1464.4 g of 25% by weight of aqueous solution of potassium hydroxide (potassium hydroxide: 6.52 mol) and 164.7 g of methanol. This reactor was cooled in an iced water bath set at 0° C. 600 g of the above-obtained composition containing 2,3-dichloro-1,1,1,3-tetrafluoropropane was dropped into the reactor while being stirred by a magnetic stirrer (introduction rate: 3.3 g/min.).

After 2,3-dichloro-1,1,1,3-tetrafluoropropane was entirely dropped, the temperature of the water bath was raised to 50° C. The reaction product was guided out of the reactor, condensed by a glass cooling device in which a coolant of 0° C. was circulated, and collected in a flask cooled in a dry ice-acetone bath. 1.5 hours later, the collection of composition A containing 1,2-dichloro-3,3,3-trifluoropropene was finished. The product collected in the flask provided at an exit of the cooling device was washed with water and then with a saturated saline solution. As a result, 107.3 g of composition A containing 1,2-dichloro-3,3,3-trifluoropropene was obtained.

The temperature of the water bath was raised to 75° C., and the reaction product was guided out of the reactor, condensed by a glass cooling device in which a coolant of 0° C. was circulated, and collected in a flask cooled in a dry ice-acetone bath. 1.5 hours later, the collection of composition B containing 1,2-dichloro-3,3,3-trifluoropropene was finished. The product collected in the flask provided at an exit of the cooling device was washed with water and then with a saturated saline solution. As a result, 109.3 g of composition B containing 1,2-dichloro-3,3,3-trifluoropropene was obtained.

The organic substance remaining in a pot in the reactor was washed with water and then with a saturated saline solution. As a result, 215.5 g of composition C containing 1,2-dichloro-3,3,3-trifluoropropene was obtained.

The obtained compositions A, B and C containing 1,2-dichloro-3,3,3-trifluoropropene were analyzed by gas chromatography. Compositions A, B and C contained cis-1,2-dichloro-3,3,3-trifluoropropene at contents of 11.4%, 54.0% and 6.6%, respectively. The yield of 1,2-dichloro-3,3,3-trifluoropropene (total yield of the cis isomer and the trans isomer) was 16.1%.

Comparative Example

A 500 ml round-bottom three-neck glass flask equipped with a glass cooling device in which a coolant of 0° C. was circulated, a glass trap cooled in a dry ice-acetone bath adjusted to −78° C., and a glass protective tube for receiving a thermocouple was supplied with 40.30 g (0.20 mol) of 1,1,2-trichloro-3,3,3-trifluoropropane, 32.00 g (0.57 mol) of potassium hydroxide, 0.68 g of tetrabutylammonium bromide, and 96.01 g of water. These compounds were stirred by a magnetic stirrer while being cooled to be dissolved. After the dissolution, the inner temperature of the flask was raised to 30° C. in a water bath, the flask was kept at this temperature for 2 hours and then the flask was cooled. The reaction was finished without the reaction product being extracted. The reaction product was cooled in the recovery grass trap cooled in the dry ice-acetone bath provided at an exit of the condenser, and 30.84 g of liquefied reaction product was collected.

The collected liquid was analyzed by gas chromatography. The reaction product was not 1,2-dichloro-3,3,3-trifluoropropene, but was 1-chloro-3,3,3-trifluoropropyne. The purity of the obtained 1-chloro-3,3,3-trifluoropropyne was 97.6%, and the yield of 1-chloro-3,3,3-trifluoropropyne was 74.0%.

The following is understood from a comparison of examples 1 through 5 against the comparative example. According to the method of the present invention, by which 1,2-dichloro-1-halogeno-3,3,3-trifluoropropane is reacted with a base in a liquid phase, and 1,2-dichloro-3,3,3-trifluoropropene generated by the reaction is extracted to the outside of the reaction system to be recovered while the reaction is continued, 1,2-dichloro-3,3,3-trifluoropropene as the target compound is obtained at a high yield. By contrast, in the comparative example, in which 1,2-dichloro-3,3,3-trifluoropropene is not extracted to the outside of the reaction system, the reaction is excessively advanced to even generate a propyne, and thus 1,2-dichloro-3,3,3-trifluoropropene is not recovered. As can be seen from a comparison of examples 1 and 2 against examples 3 through 5, the yield of 1,2-dichloro-3,3,3-trifluoropropene is higher in the case where neither a phase transfer catalyst nor a compatibilizer is used than in the case where a phase transfer catalyst and/or a compatibilizer is used. A conceivable reason for this is that in the case where neither a phase transfer catalyst nor a compatibilizer is used, generation of a reaction byproduct such as 1-chloro-3,3,3-trifluoropropyne or the like is suppressed, and also dissolution of 1,2-dichloro-3,3,3-trifluoropropene in the aqueous phase is suppressed. Thus, 1,2-dichloro-3,3,3-trifluoropropene is obtained at a higher selectivity and a higher yield in the case where neither a phase transfer catalyst nor a compatibilizer is used than in the case where a phase transfer catalyst and/or a compatibilizer is used.

As can be seen from a comparison of examples 1 through 5 against example 6, 1,2-dichloro-3,3,3-trifluoropropene as the target compound is obtained at a higher yield in the case where a compound represented by formula [1] in which X is Cl (1,1,2-trichloro-3,3,3-trifluoropropane) is used as the material compound than in the case where a compound represented by formula [1] in which X is F (2,3-dichloro-1,1,1,3-tetrafluoropropane) is uses as the material compound. Therefore, it is understood that in the method for producing 1,2-dichloro-3,3,3-trifluoropropene of the present invention, a compound represented by formula [1] in which X is Cl (1,1,2-trichloro-3,3,3-trifluoropropane) is preferable as the material compound.

According to the present invention, 1,2-dichloro-3,3,3-trifluoropropene is obtained at a high yield by a simple method. Thus, the present invention provides a method for producing 1,2-dichloro-3,3,3-trifluoropropene easily and in an industrial scale.

1,2-dichloro-3,3,3-trifluoropropene, which is a target compound of the present invention, is usable as a heat transfer medium usable for a heat pump cycle or a rankine cycle, a functional material such as a cleaner or the like, a physiologically active substance, an intermediate of a functional material, or a monomer of a polymer compound.

The invention claimed is:

1. A method for producing 1,2-dichloro-3,3,3-trifluoropropene comprising:

reacting 1,2-dichloro-1-halogeno-3,3,3-trifluoropropane represented by formula [1] as shown below with a base in a liquid phase; and extracting the generated 1,2-dichloro-3,3,3-trifluoropropene to the outside of a reaction system to recover while the reaction is continued:

[Chemical formula 1]

Formula [1]:

(in the formula, X represents fluorine, chlorine or bromine).

2. A method according to claim 1, wherein the reaction of the 1,2-dichloro-1-halogeno-3,3,3-trifluoropropane with the base is caused with neither a phase transfer catalyst nor a compatibilizer being present.

3. A method according to claim 1, wherein the base is at least one inorganic base selected from the group consisting of alkaline metal alkoxides, carbonates of alkaline metals, carbonates of alkaline earth metals, hydroxides of alkaline metals, and hydroxides of alkaline earth metals.

4. A method according to claim 1, wherein the 1,2-dichloro-1-halogeno-3,3,3-trifluoropropane is 1,1,2-trichloro-3,3,3-trifluoropropane.

* * * * *